(12) United States Patent
Yang et al.

(10) Patent No.: US 10,913,788 B2
(45) Date of Patent: Feb. 9, 2021

(54) PHARMACEUTICAL COMPOSITION FOR PREVENTING OR TREATING DRY EYES

(71) Applicant: EYEBIO KOREA, Busan (KR)

(72) Inventors: Jae Wook Yang, Busan (KR); Hye Sook Lee, Busan (KR); Chae Eun Kim, Busan (KR); Kun Moo Lee, Busan (KR)

(73) Assignee: EYEBIO KOREA, Busan (KR)

( * ) Notice: Subject to any disclaimer, the term of this patent is extended or adjusted under 35 U.S.C. 154(b) by 235 days.

(21) Appl. No.: 15/748,622

(22) PCT Filed: Nov. 24, 2015

(86) PCT No.: PCT/KR2015/012678
§ 371 (c)(1),
(2) Date: Jan. 29, 2018

(87) PCT Pub. No.: WO2017/018613
PCT Pub. Date: Feb. 2, 2017

(65) Prior Publication Data
US 2019/0002528 A1    Jan. 3, 2019

(30) Foreign Application Priority Data

Jul. 30, 2015   (KR) .................. 10-2015-0108069

(51) Int. Cl.
| | | |
|---|---|---|
| *C07K 14/78* | (2006.01) | |
| *A61K 38/08* | (2019.01) | |
| *A61P 27/04* | (2006.01) | |
| *A61K 9/48* | (2006.01) | |
| *A61K 38/39* | (2006.01) | |
| *A61K 9/00* | (2006.01) | |

(52) U.S. Cl.
CPC ............ *C07K 14/78* (2013.01); *A61K 9/0048* (2013.01); *A61K 38/08* (2013.01); *A61P 27/04* (2018.01); *A61K 38/39* (2013.01)

(58) Field of Classification Search
CPC ...... A61K 38/08; A61K 9/0048; A61K 38/39; C07K 14/78; A61P 27/04
See application file for complete search history.

(56) References Cited

U.S. PATENT DOCUMENTS

| | | |
|---|---|---|
| 5,955,578 A | 9/1999 | Pierschbacher et al. |
| 2008/0269119 A1 | 10/2008 | Griffith et al. |
| 2009/0131303 A1 | 5/2009 | Hong et al. |
| 2010/0173868 A1 | 7/2010 | Petito et al. |
| 2010/0317586 A1 | 12/2010 | Babizha Yev |
| 2016/0215018 A1* | 7/2016 | Yang ............... C07K 14/78 |

FOREIGN PATENT DOCUMENTS

| | | | | |
|---|---|---|---|---|
| KR | 10-2014-0099526 A | | 8/2014 | |
| KR | 10-2016-0079983 A | * | 7/2016 | ............ C07K 14/78 |
| WO | 2009-064983 A1 | | 5/2009 | |

OTHER PUBLICATIONS

KR 10-2016-0079983 A machin translation, pp. 1-8, accessed Feb. 21, 2019.*
Hessen et al, Dry Eye: an Inflammatory Ocular Disease, J Ophthalmic Vis Res, 2014, 9, pp. 240-250.*
Facts about Dry Eye, from https://nei.nih.gov/health/dryeye/dryeye, Jul. 2017, pp. 1-4.*
Human collagen type I alpha 1, from https://www.ncbi.nlm.nih.gov/protein/CAA67261.1, pp. 1-3, accessed Feb. 22, 2019.*
COL1A1 gene, from https://ghr.nlm.nih.gov/gene/COL1A1, Feb. 19, 2019, pp. 1-7.*
Van den Steen et al, Generation of Glycosylated Remnant Epitopes from Human Collagen Type II by Gelatinase B, Biochemistry, 2004, 43, pp. 10809-10816.*
Human collagen type II alpha 1, from https://www.ncbi.nlm.nih.gov/protein/CAA34683.1, pp. 1-3, accessed Feb. 25, 2019.*
International Search Report for PCT/KR2015/012678 dated Apr. 18, 2016 from Korean Intellectual Property Office.

* cited by examiner

*Primary Examiner* — Li N Komatsu
(74) *Attorney, Agent, or Firm* — Revolution IP, LLC

(57) ABSTRACT

The present invention relates to a pharmaceutical composition for preventing or treating dry eye, the pharmaceutical composition including, as an active component, a novel peptide is disclosed, wherein it is confirmed that the peptide has effects on improving tear production and corneal surface smoothness for dry eyes induced by desiccation stress and suppressing detachment of corneal epithelial cells, reduction in conjunctival goblet cells, and generation of inflammatory factors, thereby applying a composition including the peptide as an active component to the pharmaceutical composition for preventing or treating dry eye.

6 Claims, 5 Drawing Sheets

Specification includes a Sequence Listing.

SEQUENCE LISTING

```
<160> NUMBER OF SEQ ID NOS: 2

<210> SEQ ID NO 1
<211> LENGTH: 5
<212> TYPE: PRT
<213> ORGANISM: Artificial Sequence
<220> FEATURE:
<223> OTHER INFORMATION: peptide

<400> SEQUENCE: 1

Gly Asp Arg Gly Asp
1               5

<210> SEQ ID NO 2
<211> LENGTH: 9
<212> TYPE: PRT
<213> ORGANISM: Artificial Sequence
<220> FEATURE:
<223> OTHER INFORMATION: peptide
```

```
<400> SEQUENCE: 2

Gly Gln Asp Gly Leu Ala Gly Pro Lys
1               5
```

PHARMACEUTICAL COMPOSITION FOR PREVENTING OR TREATING DRY EYES

CROSS REFERENCE TO PRIOR APPLICATIONS

This application is a National Stage Application of PCT International Patent Application No. PCT/KR2015/012678 filed on Nov. 24, 2015, under 35 U.S.C. § 371, which claims priority to Korean Patent Application No. 10-2015-0108069 filed on Jul. 30, 2015, which are all hereby incorporated by reference in their entirety.

TECHNICAL FIELD

The present disclosure relates to a pharmaceutical composition for preventing or treating dry eye, the pharmaceutical composition including a novel peptide as an active component.

BACKGROUND ART

Dry eye is a disease having an increasing incidence rate with age, and more particularly, it is reported that about 6% of the population aged 40s shows symptoms of dry eye, and that the incidence of dry eye increases to 15% with age such that about 25% of the population aged 65 or more shows symptoms of dry eye.

Dry eye causes ocular surface damages due to failure of the balance of tear components caused by a lack of tears or excessive evaporation of tears, and is a disease associated with symptoms such as blurred vision and eye irritation caused by a foreign matter or dry feeling. Such dry eye symptoms decrease functional vision and make difficulties in performing routine work such as driving, reading, and watching television, and thus they affect the quality of life.

In most cases of dry eye, disorders of cornea/conjunctiva may be caused by an abnormality of at least one of an oil layer, a water layer, and a mucous layer that complement a tear film. In particular, the abnormality of the mucous layer causes a severe corneal disorder. Dry eye increases penetrability of fluorescein-tagged corneal epithelial cells, conjunctival modifications, and damages to goblet cells, thereby causing pathological changes in the epithelial cells of the corneal surface. Accordingly, corneal disorders or corneal epithelial erosions, corneal ulcers, and even ocular inflammation may be caused, and in some cases, corneal transplantation may be also required.

A dry eye therapy that is currently used the most includes prescription for topical application of artificial tears containing, as a substituent of mucin, a viscoelastic compound such as methyl cellulose, chondroitin sulfate, and hyaluronic acid. However, such a viscoelastic compound is physically and physiologically different from mucin, and thus, its efficacy on the therapy is limited.

DETAILED DESCRIPTION OF THE INVENTION

Technical Problem

The present invention provides a pharmaceutical composition including a novel peptide as active component for preventing or treating dry eye, wherein dry eye can be prevented or treated by suppressing or improving pathological changes of corneal epithelial cells, the pathological changes including a decrease in tear volume of eyes, corneal surface irregularities, and loss of conjunctival goblet cells.

Technical Solution

The present invention provides a pharmaceutical composition for preventing or treating dry eye, the pharmaceutical composition comprising, as an active component, a peptide having an amino acid sequence of SEQ ID NO: 1 or 2.

Advantageous Effects of the Invention

According to the present invention, a novel peptide is found to have effects on the improvement of tear production and corneal surface smoothness in dry eyes having desiccation stress and on the suppression of detachment of corneal epithelial cells, reduction of conjunctival goblet cells, and production of inflammatory factors. Thus, a composition including the novel peptide as an active component can be applied to a pharmaceutical composition for preventing or treating dry eye.

DESCRIPTION OF THE DRAWINGS

FIG. 2 shows results confirming the effects of GDRGD (SEQ ID NO: 1) and GQDGLAGPK (SEQ ID NO: 2) peptides on distortion of the corneal surface, wherein FIG. 2A shows eye image results for each group prepared by treating NOD.B10.H2b mice with PBS, peptide I, peptide II, and HA, wherein desiccation stress is removed from the NOD.B10.H2b mice (scale bar=1 mm), and FIG. 2B shows quantitative results confirming changes in corneal smoothness scores in mice each treated with PBS, peptide I, peptide II, and HA, wherein the in corneal smoothness scores are quantified in terms of mean±standard deviation (*$p<0.05$ vs. DS 10D group);

FIG. 3 shows results confirming the effects of GDRGD (SEQ ID NO: 1) and GQDGLAGPK (SEQ ID NO: 2) peptides on detachment of corneal epithelial cells, wherein FIG. 3A shows results of the haematoxylin and eosin (H&E) stain confirming the extent of detachment of the corneal epithelial cells on corneas of the NOD.B10.H2b mice that are treated by administering PBS, peptide I, peptide II, and hyaluni for 10 days thereto (scale bar=100 µm), and FIG. 3B shows quantitative results showing the extent of detachment of the corneal epithelial cells as being quantified in terms of mean±standard deviation (*$p<0.05$ vs. DS 10D group);

FIG. 4 shows results confirming the effects of peptide I (i.e., GDRGD (SEQ ID NO: 1)) and peptide II (i.e., GQDGLAGPK (SEQ ID NO: 2)) on distribution of conjunctival goblet cells, wherein FIG. 4A shows results of the periodic acid-Schiff (PAS) stain on conjunctiva of NOD.B10.H2b mice that are treated by administering PBS, peptide I, peptide II, and hyaluni thereto (scale bar=200 µm), and FIG. 4B shows quantitative results showing the extent of distribution of conjunctival goblet cells as being quantified in terms of mean±standard deviation (*p<0.05 vs. DS 10D group)

BEST MODE

The present invention provides a pharmaceutical composition for preventing or treating dry eye, the pharmaceutical composition including, as an active component, a peptide having an amino acid sequence of SEQ ID NO: 1 or 2.

The peptide having the amino acid sequence of SEQ ID NO: 1 may be derived from collagen type I α1, and the peptide having the amino acid sequence of SEQ ID NO: 2 may be derived from collagen type II α1.

In further detail, the peptide having the amino acid sequence of SEQ ID NO: 1 or 2 may be a peptide isolated from a chondrocyte-derived extracellular matrix (CDEM), wherein the CDEM may be isolated from a CDEM that are formed as being secreted from a cartilage tissue and/or a chondrocyte of an animal. The animal may be selected from pigs, horses, cattle, sheep, goats, and monkeys, but the animal is not limited thereto.

The peptide having the amino acid sequence of SEQ ID NO: 1 or 2 may recover a production of tears that have been reduced by desiccation stress and an imbalance in a corneal surface, and may suppress detachment of corneal epithelial cells and production of inflammatory factors.

Figure 1:
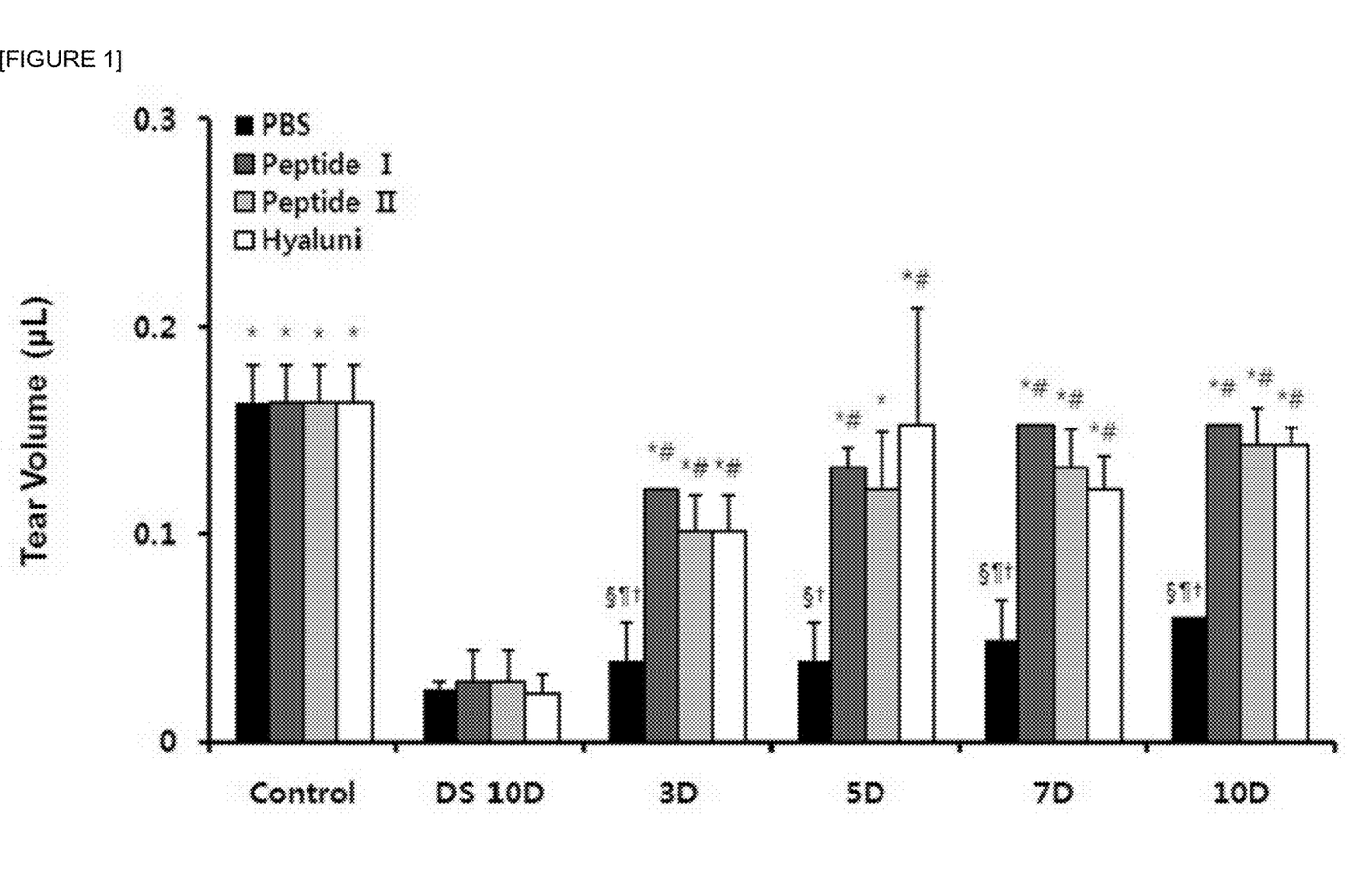
FIG. 1 shows quantitative results confirming changes in tear volume in eyes of NOD.B10.H2$^b$ mice in a PBS group, a peptide I group, a peptide II group, and a hyaluni (HA) group, wherein desiccation stress is removed from the NOD.B10.H2$^b$ mice, and the tear volume in eyes of the NOD.B10.H2$^b$ mice was measured and quantified in terms of mean±standard deviation after administering PBS, peptide I, peptide II, and HA into the eye balls of the NOD.B10.H2$^b$ mice for 3, 5, 7, and 10 days (*$p<0.05$ vs. DS 10D group. # $p<0.05$ vs. PBS group. § $p<0.05$ vs. peptide I group. ¶$p<0.05$ vs. peptide II group. †$p<0.05$ vs. hyaluni group)

In an exemplary embodiment of the present invention, as shown in FIG. 1, the tear volume of NOD.B10.H2b mice in a test group (e.g., the DS 10 D group: 0.03±0.01 μL, p<0.05) is significantly reduced by about 86% compared to the tear volume of NOD.B10.H2b mice in a control group (i.e., 0.16±0.02 μL), depending on desiccation stress. The tear volume of NOD.B10.H2b mice in a test group, in which desiccation stress is removed from the animal model and peptide I (i.e., GDRGD (SEQ ID NO: 1)) and peptide II (i.e., GQDGLAGPK (SEQ ID NO: 2)) are treated therewith, is increased by about 2.52 times (p<0.05) as much as that of a control animal model treated with PBS. In this regard, it is confirmed that the results of FIG. 1 show similar levels with a case where the animal model is treated with HA, which is a therapeutic agent for dry eye syndrome.

Based on the results above, it is confirmed that peptides I and II can significantly treat the tear volumes that are decreased in dry eyes, thereby being capable of recovering the tear volumes up to normal tear volumes.

The peptide having the amino acid sequence of SEQ ID NO: 1 or 2 may be included in an amount ranging from about 0.1 to about 50 parts by weight based on a total of 100 parts by weight of the pharmaceutical composition.

The pharmaceutical composition of the present invention may be formulated as one selected from the group consisting of eye drops, injections, granules, tablets, pills, capsules, gels, syrups, suspensions, emulsions, drips, and liquids, but the formulation is not limited thereto.

In another exemplary embodiment of the present invention, the pharmaceutical composition including, as an active component, the peptide having the amino acid sequence of SEQ ID NO: 1 or 2 for preventing or treating an ocular surface disease may further include at least one appropriate additive selected from the group consisting of carriers, excipients, disintegrating agents, sweetening agents, coating agents, sweeling agents, glidants, flavoring agents, antioxidants, buffers, bacteriostatic agents, diluents, dispersants, surfactants, binders, and lubricants that are typically used in preparation of a composition in the art.

In further detail, examples of the carriers, the excipients, and diluents include lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate, and mineral oil. Examples of solid formulations for oral administration include tablets, pills, powders, granules, and capsules. Such solid formulations may be prepared by mixing the pharmaceutical composition with at least one excipient, e.g., starch, calcium carbonate, sucrose or lactose, or gelatin. Also, a lubricant such as magnesium stearate or talc may be used in addition to a simple excipient. Examples of the liquids for oral administration include suspensions, material solutions, emulsions, and syrups, and the liquids may further include various types of excipient including wetting agents, sweeteners, flavoring agents and preservatives, in addition to simple and commonly used diluents, such as water or liquid paraffin. Examples of formulations for parenteral administration include sterilized aqueous solutions, non-aqueous solvents, suspensions, emulsions, lyophilized preparations, and suppositories. Examples of the non-aqueous solvents and the suspensions include propylene glycol, polyethylene glycol, vegetable oil including olive oil, and injectable esters including ethyl oleate. Bases for the suppositories may be witepsol, macrogol, TWEEN® 61, cacao butter, Laurin, or glycerogelatine.

In an exemplary embodiment of the present invention, the pharmaceutical composition may be administered to a subject via a conventional route of administration selected from intravenous, intraarterial, intraperitoneal, intramuscular, intrasternal, percutaneous, intranasal, inhalation, topical, rectal, oral, intraocular, or subcutaneous administration.

A desired dose of the peptide having the amino acid sequence of SEQ ID NO: 1 or 2 to the subject may differ according to the subject's conditions and weight, types and severity of a disease, a drug form, an administration route, and an administration period, and may be appropriately selected by one of ordinary skill in the art. In an exemplary embodiment of the present invention, a daily dose of the peptide having the amino acid sequence of SEQ ID NO: 1 or 2 may be in a range of about 0.01 to about 200 mg/kg, for example, about 0.1 to about 200 mg/kg, for example, about 0.1 to about 100 mg/kg, but the daily dose is not limited thereto. Administration may be performed once a day or several times a day, but the number of administration is not limited thereto.

The term 'subject' as used herein may refer to mammals including humans, but the 'subject' is not limited thereto.

MODE OF THE INVENTION

Hereinafter, the present disclosure is described in detail with reference to Examples. However, Examples shown and described herein are illustrative examples of the present invention and are not intended to otherwise limit the scope of the inventive concept in any way; rather, these Examples are provided so that the present disclosure will be thorough and complete, and will fully convey the concept of the inventive concept to those skilled in the art.

<Experimental Example 1> Synthesis of Peptides

Peptides used in all experiments were collagen type I α1 based peptide GDRGD (hereinafter, referred to as 'peptide I', SEQ ID NO: 1) and collagen type II α1 based peptide GQDGLAGPK (hereinafter, referred to as 'peptide II', SEQ ID NO: 2), which were synthesized from PEPTRon (Daejeon, Korea).

<Experimental Example 2> Experimental Animals and Preparation of Dry Eye Animal Models NOD.B10.H2$^b$ mice were purchased from Jackson Laboratory (Bar Harbor, Me., USA). Experiments on animals were performed according to the guidelines for animal experiments of Inje University College of Medicine (No.; 2014-029) and the ARVO statement for the use of animals in ophthalmic and vision research. 12-to-16-week-old NOD.B10.H2$^b$ mice underwent desiccation stress as being exposed to an air draft from a fan at an ambient humidity of about 40% to 50% for 18 hours per day, and then, were subjected to subcutaneous injection of 0.5 mg/0.2 mL of muscarinic receptor blockers. Also, the mice were injected with scopolamine hydrobromide (Sigma-Aldrich, St. Louis, Mo.) alternatively on hindquarters 4 times per day (9 AM, 12 PM, 3 PM, and 6 PM) for 10 days. During these experiments, behaviors and food and water intakes of the mice were not restricted. 10 days later, the mice were euthanized.

10 days after the mice underwent desiccation stress, the scopolamine injection was halted, and then, the mice newly had environments with normal humidity and temperature. After the desiccation stress was removed, the mice were divided into a peptide I group or a peptide II group, wherein 10 mg/ml of peptide I or 10 mg/ml of peptide II was dissolved in PBS and 5 μL of PBS was instilled into eyeballs of the mice 5 times per day for 10 days. In addition, 5 μL of PBS or 5 μL of 0.1% HA were instilled into eyeballs of the mice in a control group, i.e., a PBS group or a hyaluni (HA) group, 5 times a day for 10 days. In each group, both eyes of each of 5 mice were used to conduct the experiments in a repetitive manner.

<Example 1> Effects of Peptides on Tear Production

Extents of tear production were measured with phenol red-impregnated cotton threads (Zone-Quick; Oasis, Glendora, Calif.), as previously described (Villareal A L, Farley W, Pflugfelder S C. Effect of topical ophthalmic epinastine and olopatadine on tear volume in mice. Eye Contact Lens. 2006; 32(6):272-276). The threads were held medical tweezers and placed in the lateral canthus for 20 seconds. The tear volumes were expressed as millimeter (mm) of wet thread that had been turned red by the tears, as measured under a microscope (SZX7; Olympus corp, Tokyo, Japan).

The tear fluid uptakes measured in millimeters were compared to a standard curve that was prepared from cotton threads with known uptake volumes of a stock basic solution (1,500 mL of 0.9% saline and 5 mL of 5 N NaOH) over 20 seconds that were within the range that would be expected for mouse tears.

Consequently, as shown in FIG. 1, the desiccation stress significantly decreased the tear production by about 86% (DS 10 D group, 0.03±0.01 μL, p<0.05) compared to the tear production in the normal group (0.16±0.02 μL). After the removal of the desiccation stress in the dry eye mice, it was confirmed that the peptide I group and the peptide II group showed increased tear production by up to about 2.52-fold (p<0.05) compared to the control group (i.e., the PBS group). These results were similar with a case where the animal model was treated with HA, which is a therapeutic agent for dry eye syndrome.

Thus, it was confirmed that peptides I and II can significantly treat the tear volumes that were decreased in dry eyes, thereby being capable of recovering the tear volumes up to normal tear volumes.

<Example 2> Effects of Peptides on Corneal Surface Irregularities

1. Evaluation of Corneal Surface Smoothness

The corneal surface smoothness in the experimental groups (i.e., the peptide I group and the peptide II group) was evaluated in comparison with that in the control groups (i.e., the PBS group and the HA group). Immediately after the mice in two experimental groups were euthanized, reflected images of the white ring of a fiber optic ring illuminator of a stereoscopic microscope (SZX7; Olympus) were obtained.

The corneal smoothness was evaluated by grading irregularities of the white ring as reflected off the corneal epithelial cells in the digital images. The corneal irregularity severity scores were calculated using a five-point scale on the basis of the number of distorted quarters in the reflected ring and were graded as follows: 0, no distortion; 1, distortion in one quarter; 2, distortion in two quarters; 3, distortion in three quarters; 4, distortion in all four quarters; and 5, distortion so severe that no section of the ring was recognized.

Figure 2:
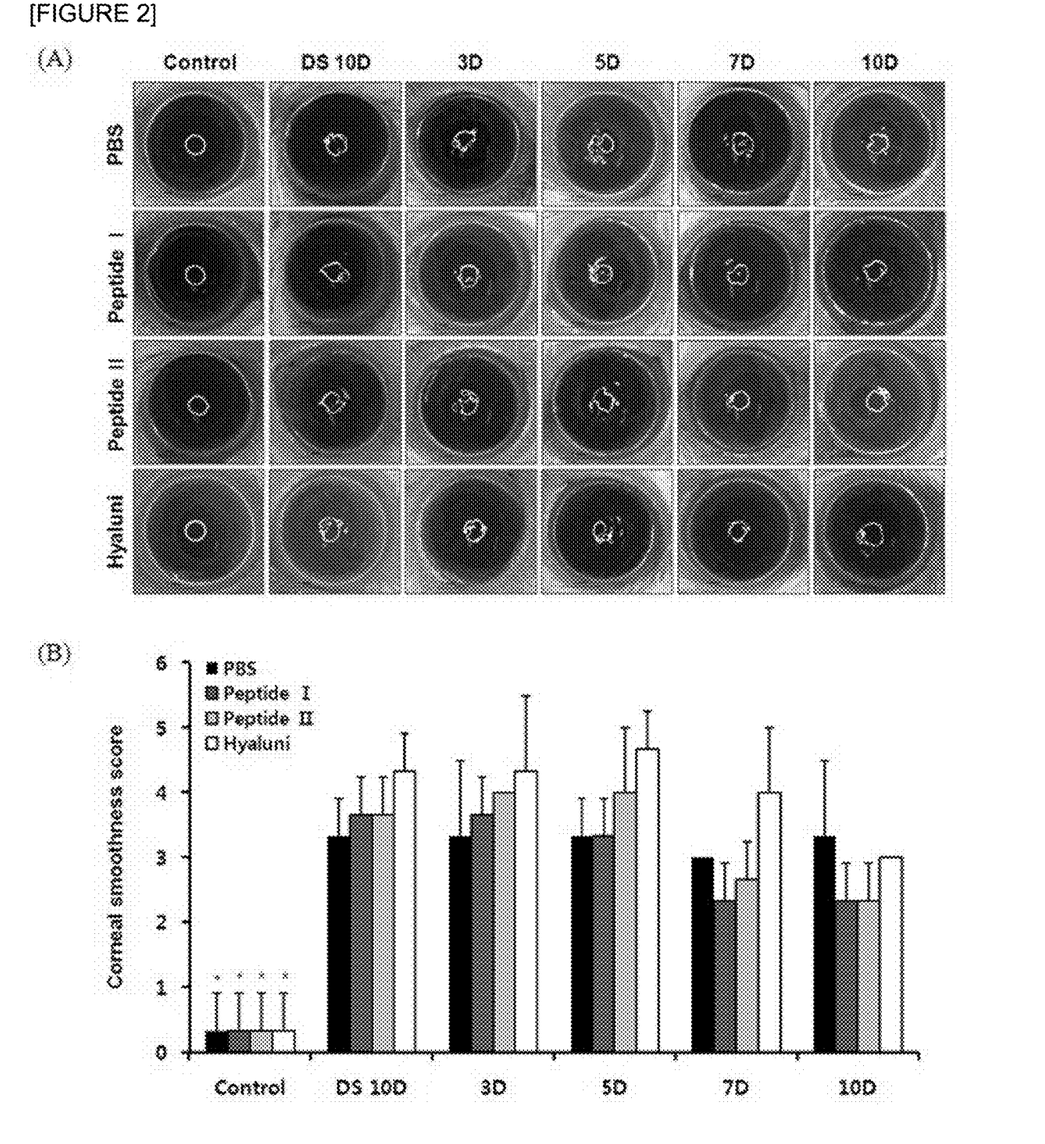

2. Effects of GDRGD (SEQ ID NO: 1) and GQDGLAGPK (SEQ ID NO: 2) on Improvement of the Corneal Irregularities As a result of quantifying the extent of the corneal irregularities of the dry eye mice according to the method for evaluating the corneal surface smoothness, as shown in FIG. 2, it was confirmed that the desiccation stress increased to about 9.02-fold the corneal surface irregularity of the mice, which had undergone the desiccation stress for 10 days, compared to the corneal surface irregularity of normal corneas. However, no distortion of the corneal surface was found in the PBS group at 3, 5, 7, and 10 days, wherein the peptide groups improved the corneal irregularity over time compared to the PBS. In addition, it was confirmed that the peptide groups showed better effects on the improvement of the distortion of the corneal surface compared to the HA group using a therapeutic agent for dry eye syndrome, HA.

<Example 3> Confirmation of Effects of Peptides on Corneal Cells

1. Immunohistochemistry

The eyes and adnexa of the mice in the control groups (i.e., the PBS group and the HA group) and the experimental groups (i.e., the peptide I group and the peptide II group) were surgically excised, fixed in 10% formalin, and embedded in paraffin and an OCT compound.

6 μm sections of the tissue samples were stained with haematoxylin and eosin (H&E) and periodic acid-Schiff (PAS) reagent.

5 animals in each group were subjected to the staining as described above, and then, were examined and photographed with a virtual microscope (NanoZoomer 2.0 RS, Hamamatsu, Japan).

Figure 3:
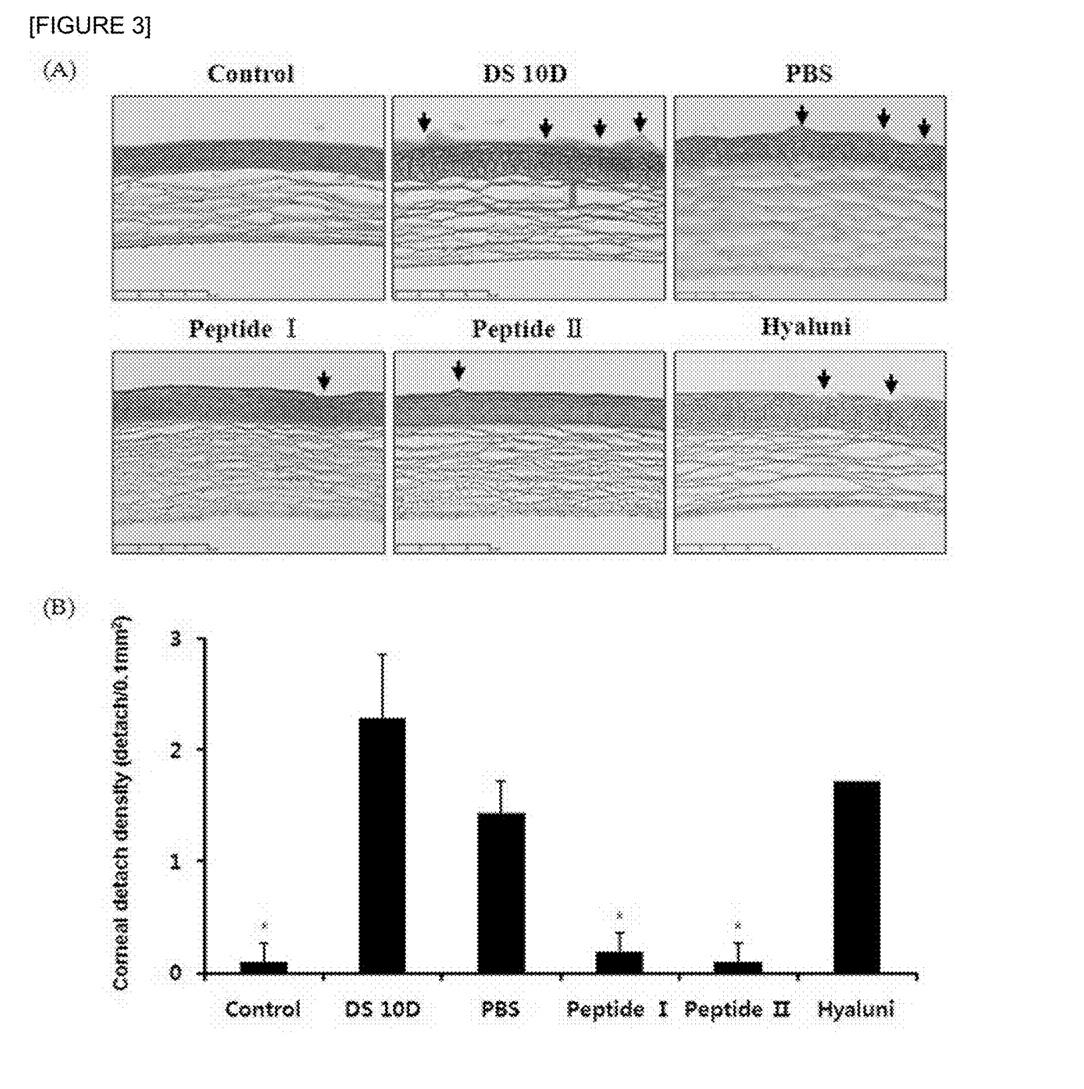

2. Effects of GDRGD (SEQ ID NO: 1) and GQDG-LAGPK (SEQ ID NO: 2) on Detachment of Corneal Epithelial Cells As a result of staining the corneas of the NOD.B10.H2[b] mice, as shown in FIG. 3, it was confirmed that the desiccation stress increased to about 4.17-fold detachment of corneal epithelial cells ($2.29\pm0.61/0.1$ mm$^2$, $p<0.05$). This alteration by desiccation stress was not decreased by PBS ($1.43\pm0.34/0.1$ mm$^2$) or HA ($1.71\pm0.00/0.1$ mm$^2$). In contrast, the number of the detached corneal epithelial cells was significantly decreased to about $0.19\pm0.14/0.1$ mm$^2$ by peptide I. In particular, the peptide II group decreased the detachment of the corneal epithelial cells down to about 4-fold compared to the control groups, and it was confirmed that peptides I and II exhibited a reduction in the number of the detached corneal epithelial cells similar to normal corneas.

3. Effects of GDRGD (SEQ ID NO: 1) and GQDG-LAGPK (SEQ ID NO: 2) on Distribution of Conjunctival Goblet Cells The distribution of the conjunctival goblet cells in the dry eye mice were observed following peptide I, peptide II, and HA instillation.

Figure 4:
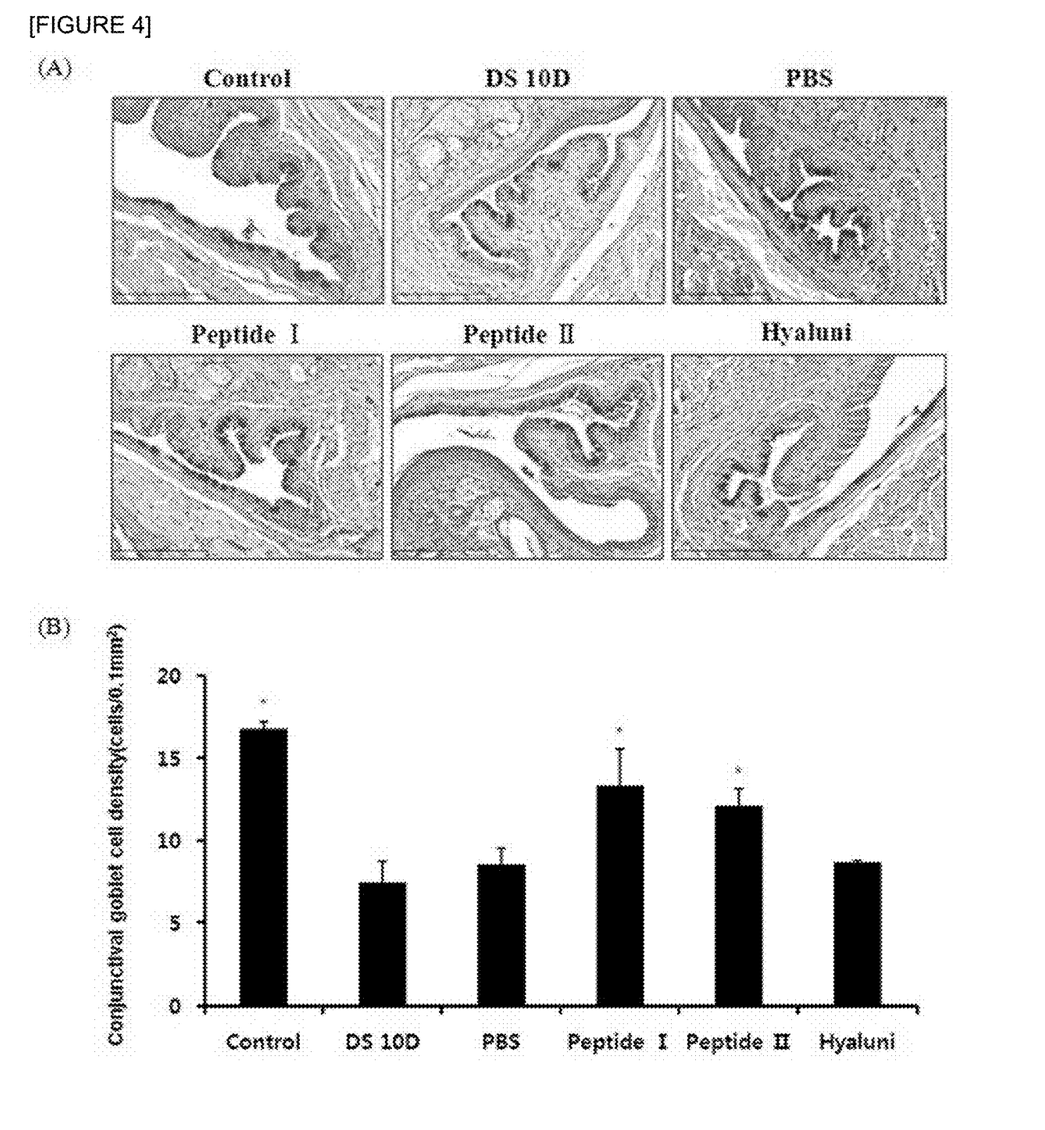

Consequently, as shown in FIG. 4, it was confirmed that the conjunctival goblet cells were decreased by about 44.32% ($7.43\pm1.52/0.1$ mm$^2$, $p<0.05$) in the experimental groups compared to normal conjunctival goblet cells. No effect on the distribution of the conjunctival goblet cells was found in the PBS group or the HA group. However, the conjunctival goblet cells that were decreased by the desiccation stress were significantly increased in the peptide I group and the peptide II group to about 1.8-fold ($13.33\pm2.41/0.1$ mm$^2$, $p<0.05$) and about 1.63-fold ($12.10\pm1.11/0.1$ mm$^2$, $p<0.05$), respectively.

<Example 4> Anti-Inflammatory Effects of Peptides

To evaluate effects of the peptides on expression of inflammatory markers in the dry eye mice, the conjunctiva was immunostained with TNF-α, ICAM-1, VCAM-1, MMP-2, and MMP-9, so as to perform the immunohistochemical analysis.

First, the tissue (i.e., conjunctiva) was cut into sections having a thickness of 6 μm. The sections were fixed in 3.5% paraformaldehyde, embedded in 0.1% Triton X-100, inactivated with 2% bovine serum solution (BSA; all from sigma), and then, allowed to have a reaction with primary antibodies, such as anti-TNF-α, anti-MMP-2 (1:1000; all from Abcam Inc, Cambridge, Mass.), anti-MMP-9 (1:1000; Lifespan Biosciences Inc, Seattle, Wash.), anti-ICAM-1, and anti-VCAM-1 (1:1000; all from Bioss Inc, Woburn, Mass.) for 1 hour at room temperature. Afterwards, the sections were incubated with a secondary antibody (DAKO Corp, Glostup, Denmark) for 20 minutes. Here, immunoreactions were visualized with diaminobenzidine (DAB) chromogen, and the sections were counterstained with Mayer's hematoxylin (Sigma) for 30 seconds at room temperature. Images of the sections were photographed with a Virtual Microscope (NanoZoomer 2.0 RS, Hamamatsu, Japan).

Figure 5:
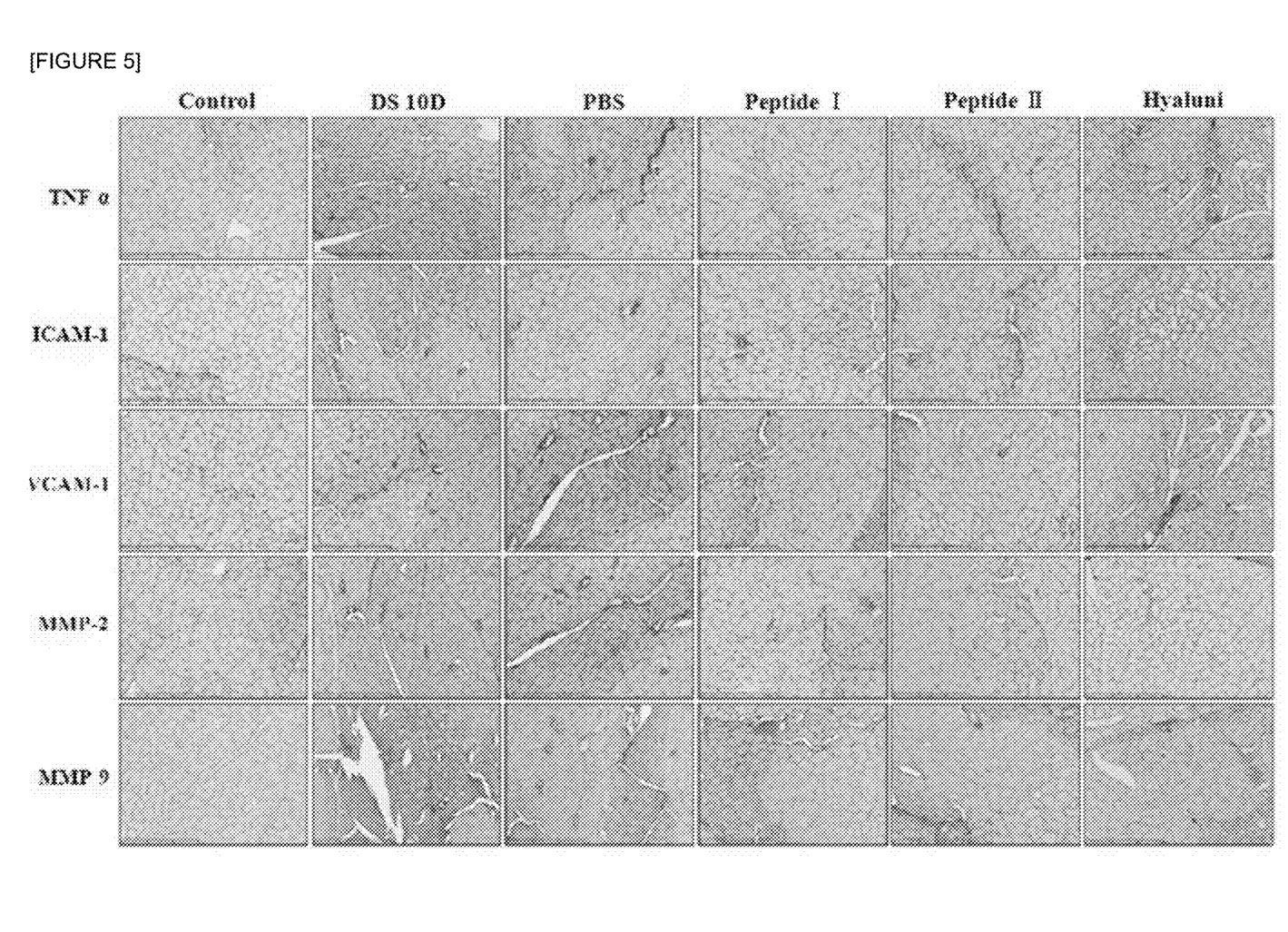
FIG. 5 shows immunohistochemical analysis results confirming the extent of expression of TNF-α, ICAM-1, VCAM-1, MMP-2, and MMP-9 in conjunctiva of NOD.B10.H2b mice, wherein the results show the extent of the inflammatory factors above in the conjunctiva of the NOD.B10.H2b mice from which desiccation stress is removed after administering PBS, peptide I, peptide II, and hyaluni for 10 days (scale bar=300 μm).

Consequently, as shown in FIG. 5, it was confirmed that desiccation stress significantly increased expression of inflammatory cytokine TNF-α and adhesion molecules including ICAM-1 and VCAM-1 in the conjunctiva. Furthermore, expression of MMP2 and MMP9 was also markedly increased in the conjunctiva. However, in the experimental groups (i.e., the peptide I group and the peptide II group), expression of these inflammatory markers in the conjunctiva was significantly decreased, and it was confirmed that such results are similar with a case where the animal model was treated with HA.

According to one or more embodiments of the present invention, a novel peptide is found to have effects on the improvement of tear production and corneal surface smoothness in dry eyes having desiccation stress and on the suppression of detachment of corneal epithelial cells, reduction of conjunctival goblet cells, and production of inflammatory factors. Thus, a composition including the novel peptide as an active component can be applied to a pharmaceutical composition for preventing or treating dry eye.

The embodiments of the present invention described above are not intended to limit the spirit of the present invention. The scope of the present invention should be construed according to the following claims, and the spirit within the scope of the claims should be construed as being included in the scope of the present invention.

The invention claimed is:

1. A method of treating dry eye in a subject in need thereof, comprising:
   providing a pharmaceutical composition comprising, as an active component, a peptide consisting of the amino acid sequence of SEQ ID NO: 1 or 2; and
   administering the pharmaceutical composition to the subject, wherein the dry eye is treated.

2. The method of claim 1, wherein the peptide consisting of the amino acid sequence of SEQ ID NO: 1 is derived from collagen type I α1.

3. The method of claim 1, wherein the peptide consisting of the amino acid sequence of SEQ ID NO: 2 is derived from collagen type II α1.

4. The method of claim 1, wherein the amount of the peptide consisting of the amino acid sequence of SEQ ID NO: 1 or 2 is in a range of 0.1 to 50 parts by weight based on a total of 100 parts by weight of the pharmaceutical composition.

5. The method of claim 1, wherein the peptide consisting of the amino acid sequence of SEQ ID NO: 1 or 2 recovers a production of tears that have been reduced by desiccation stress and an imbalance in a corneal surface, and suppresses detachment of corneal epithelial cells and production of inflammatory factors.

6. The method of claim 1, wherein the pharmaceutical composition is formulated as one selected from the group consisting of eye drops, granules, tablets, pills, capsules, gels, syrups, suspensions, emulsions, drips, and liquids.

* * * * *